United States Patent
Odagiri et al.

(10) Patent No.: US 11,168,293 B2
(45) Date of Patent: *Nov. 9, 2021

(54) CULTURE BAG, AND CULTURE APPARATUS

(71) Applicant: Dexerials Corporation, Tokyo (JP)

(72) Inventors: Hirokazu Odagiri, Sendai (JP);
Yasuyuki Kudo, Shimotsuke (JP);
Rishabh Gupta, Shimotsuke (JP); Keiji Honjo, Kiyose (JP)

(73) Assignee: Dexerials Corporation, Tokyo (JP)

( * ) Notice: Subject to any disclaimer, the term of this patent is extended or adjusted under 35 U.S.C. 154(b) by 386 days.

This patent is subject to a terminal disclaimer.

(21) Appl. No.: 15/982,170

(22) Filed: May 17, 2018

(65) Prior Publication Data

US 2018/0340141 A1    Nov. 29, 2018

(30) Foreign Application Priority Data

May 24, 2017  (JP) .............................. JP2017-103124

(51) Int. Cl.
| | | |
|---|---|---|
| *C12M 1/00* | (2006.01) | |
| *C12M 1/21* | (2006.01) | |
| *B01F 11/00* | (2006.01) | |
| *B01F 15/00* | (2006.01) | |

(52) U.S. Cl.
CPC ......... *C12M 23/14* (2013.01); *B01F 11/0017* (2013.01); *B01F 15/0085* (2013.01); *B01F 15/00844* (2013.01); *C12M 23/02* (2013.01); *C12M 23/26* (2013.01); *C12M 41/02* (2013.01); *B01F 2215/0073* (2013.01)

(58) Field of Classification Search
None
See application file for complete search history.

(56) References Cited

U.S. PATENT DOCUMENTS 7,691,625 B2 *  4/2010  Kuwabara .............. C12M 23/10
                                                                435/283.1
2011/0014689 A1 *  1/2011  Gandlur .............. B01F 11/0028
                                                                435/289.1

FOREIGN PATENT DOCUMENTS

| JP | 2010540228 A | 12/2010 |
| JP | 2014239675 A | 12/2014 |

OTHER PUBLICATIONS

Jan. 5, 2021, Notification of Reasons for Refusal issued by the Japan Patent Office in the corresponding Japanese Patent Application No. 2017-103124.

* cited by examiner

*Primary Examiner* — William H. Beisner
(74) *Attorney, Agent, or Firm* — Kenja IP Law PC

(57) ABSTRACT

Provided is a culture bag accommodating a culture fluid, the culture bag is capable of suppressing foaming in the culture fluid when oscillating the culture fluid to perform a culture, and performing a culture with high efficiency. The culture bag includes a culture space accommodating a culture fluid, the culture space being an endless space to allow the culture fluid to circulate therein, in which the culture bag has an inner surface that comes into contact with the culture fluid to be accommodated therein, the inner surface including, at least in part thereof, a first surface formed of a fine structure and a second surface formed of a structure different from that of the first structure.

19 Claims, 6 Drawing Sheets

CULTURE BAG, AND CULTURE APPARATUS

TECHNICAL FIELD

The present disclosure relates to a culture bag and a culture apparatus.

BACKGROUND

Disposable culture bags have conventionally been used for culturing microorganisms and animal and plant cells. Culture bags are typically formed of a bag body made of a flexible resin, and accommodate therein a culture fluid suspending culture targets such as cells at a given concentration (number).

When performing a culture in such culture bags, in general, culture fluids need to be favorably agitated; high agitation performance of the culture fluid allows circulation of nutrients, and maintains gas components such as oxygen and carbon dioxide being dissolved in the culture fluid, which promotes growth of culture targets, to thereby improve culture efficiency.

Various studies have been conducted to address such demand. For example, Patent Literature 1 discloses, as a technology applicable to cell culture, a mixing container provided with baffles, in which the container is oscillated along a movable axis, to thereby cause a vortex motion in the liquid in the container so as to effect efficient mixture.

CITATION LIST

Patent Literature

PTL 1: JP2010-540228A

SUMMARY

However, when the aforementioned agitation through oscillation of the mixing container is directly applied to cell culture, the culture fluid collides with the baffles in the container to create waves, and the waves catch gas therein which generates babbles and foams when the waves falling on the fluid surface. Then, the babbles and foams rupture in the culture fluid to induce an impact, which causes damage to the culture targets such as cells, affecting the culture. Accordingly, the aforementioned technology still needs to be improved in terms of suppressing the occurrence of foaming while obtaining high agitation performance as well as high culture efficiency.

It could therefore be helpful to provide a culture bag capable of suppressing the occurrence of foaming when oscillating the culture fluid to perform a culture, and performing a culture with high efficiency, and a culture apparatus including the culture bag.

The present disclosure therefore provides the followings:

<1> A culture bag including a culture space accommodating a culture fluid, in which:

the culture bag has an inner surface that comes into contact with the culture fluid to be accommodated therein, the inner surface including, at least in part thereof, a first surface formed of a fine structure and a second surface formed of a structure different from that of the first surface.

<2> The culture bag according to any of the foregoing <1>, in which the fine structure of the first surface is a first concave-convex structure having a concave-convex pattern with a height $h1$ of 200 nm or more and less than 1 mm, a width $w1$ of 200 nm or more and less than 1 mm, and a pitch $p1$ of 200 nm or more and less than 1 mm.

<3> The culture bag according to the foregoing <2>, having an aspect ratio $h1/w1$ of 0.5 or more.

<4> The culture bag according to any of the foregoing <1> to <3>, in which the structure of the second surface is a second concave-convex structure having a concave-convex pattern with a height $h2$ of 200 nm or more and less than 1 mm, a width $w2$ of 200 nm or more and less than 1 mm, and a pitch $p2$ of 200 nm or more and less than 1 mm.

<5> The culture bag according to the foregoing <4>, having an aspect ratio $h2/w2$ of 0.5 or more.

<6> The culture bag according to any of the foregoing <1> to <5>, in which more than one of the first surfaces and more than one of the second surfaces are alternately adjacent to each other.

<7> The culture bag according to any of claims 1 to 6, in which the culture space is an endless space that allows the culture fluid to circulate therein.

<8> The culture bag according to any of the foregoing <1> to <7>, in which the culture space is a doughnut-like space.

<9> A culture apparatus comprising the culture bag according to any of the foregoing <1> to <8>.

The present disclosure therefore provides: a culture bag accommodating a culture fluid to be agitated to perform a culture, the culture bag being capable of suppressing the occurrence of foaming, to thereby perform a culture with high efficiency; and a culture apparatus including the culture bag.

DETAILED DESCRIPTION

Hereinafter, the present disclosure is described in detail with reference to embodiments.

(Culture Bag)

The disclosed culture bag according to an embodiment (which may also be referred to as "culture bag of this embodiment" in below) includes a culture space for accommodating a culture fluid, the culture space having an inner surface that comes into contact with the culture fluid to be accommodated therein, the inner surface including, at least in part thereof, a first surface formed of a fine structure and a second surface different from the first surface. Here, the culture bag of this embodiment may also include: a port for supplying a mixed gas of oxygen and carbon dioxide with controlled concentration; a port for supplying or recovering the culture fluid; and a port for acquiring a sample.

Here, the "fine structure" disclosed herein refers to a structure having irregularities on the order of μm and/or on the order of nm, without including irregularities on the order of mm.

As understood from the above, the culture bag of this embodiment includes different surface structure regions adjacent to one another at least in part of the inner surface that comes into contact with the culture fluid to be accommodated therein. Accordingly, when the culture bag accommodating the culture fluid therein is oscillated, the culture fluid passes over the aforementioned different surface structure regions, resultantly causing the culture fluid to flow in various directions (vectors) at various rates, which increases the agitating performance and even allows for highly efficient culture. Further, in the culture bag of this embodiment, at least any of the aforementioned different surface structure regions is a region of fine structure. In this regard, a liquid (Newtonian fluid) passing over a fine structure body leads to a significant change in velocity at the interface between the liquid and the fine structure. As a result, the culture bag of this embodiment can further diversify the flow of the culture fluid when oscillated, to thereby further increase the culture efficiency sufficiently. Further, in the culture bag of this embodiment, the different surface structure regions are adjacent to each other, to thereby improve agitation performance, which can significantly suppress the occurrence of foaming, as compared with the case of increasing agitation performance by means of baffles or the like.

<Culture Space>

Figure 1A:
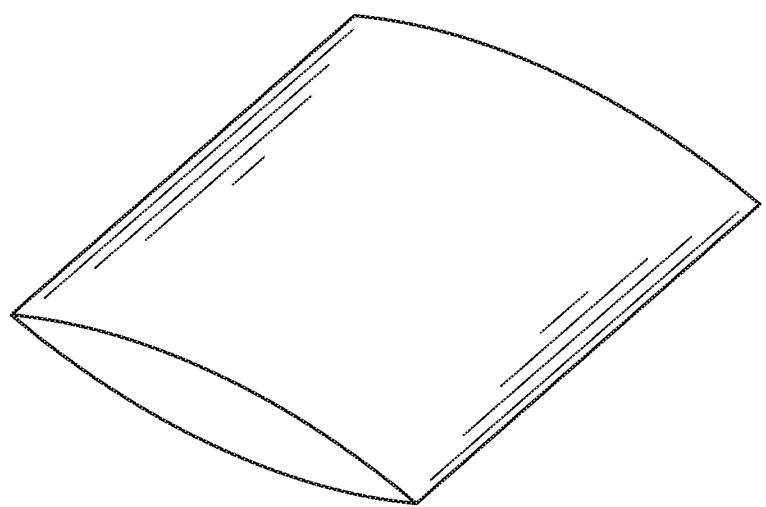
FIGS. 1A and 1B each are a schematic diagram illustrating an exemplary shape of the disclosed culture bag according to an embodiment.
Figure 1B:
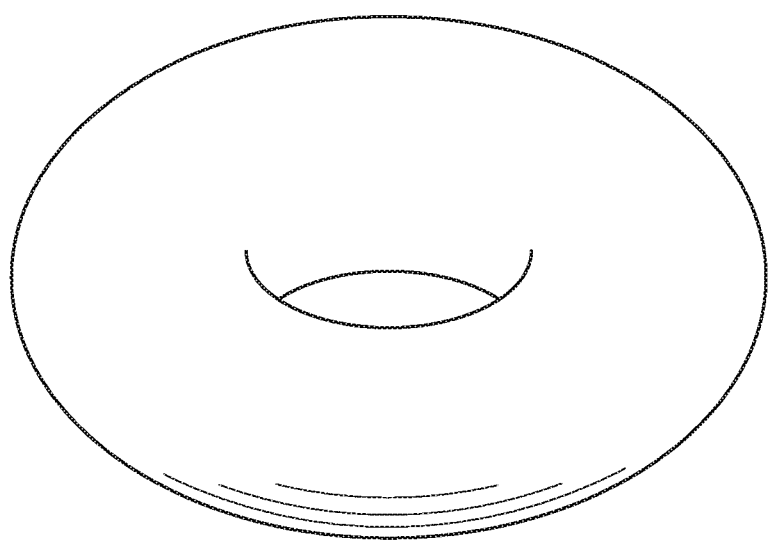

The culture bag of the embodiment includes a culture space to accommodate a culture fluid. The culture space is not particularly limited without departing from the gist of the disclosure, and may be configured as an arbitrary three-dimensional culture space, such as, for example, a substantially rectangular shape in plan view as illustrated in FIG. 1A, without departing from the gist of the disclosure. In particular, the culture space may preferably an endless space that allows the culture fluid to circulate therein. This configuration can further suppress the collision between the culture fluid and the inner surface, and further reduce waves to be generated in the culture fluid, to thereby effectively suppress the occurrence of foaming. In particular, from the same point of view, the culture space may preferably be a doughnut-like space as illustrated in FIG. 1B.

Here, the term "doughnut-like" as used herein in relation to the culture space is not limited to those being a true circle in section of the culture space taken along a line perpendicular to the circulating direction of the culture fluid, and should also include those being, for example, an oval shape or any shape defined by arbitrary arcs and line segments. Further, the term "doughnut-like" as used herein in relation to the culture space is not limited to those being a true circle in shape formed by a main circulation path of the culture fluid, and may include those being, for example, an oval shape or any shape defined by arbitrary arcs and line segments.

<Inner Surface>

In the culture bag of this embodiment, the inner surface that comes into contact with the culture fluid to be accommodated therein includes, at least in part thereof, a first surface formed of a fine structure and a second surface formed of a structure different from that of the first surface, and may further include, alternatively, an additional surface formed of a structure different from those of the first surface and the second surface. Here, whether or not an arbitrary inner surface of the culture bag corresponds to the "inner surface that comes into contact with the culture fluid to be accommodated therein" may vary depending on the amount of the culture fluid to be accommodated therein. In consideration thereof, the culture bag of this embodiment may preferably have the aforementioned first surface, the second surface, and the alternative additional surface in the inner surface at the bottom.

Further, in the culture bag of this embodiment, the structure of the inner surface not in contact with the culture fluid accommodated therein is not particularly limited.

—First Surface—

Figure 2:
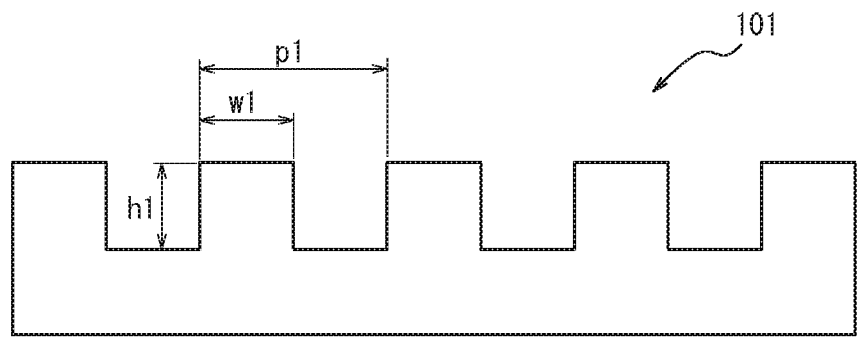
FIG. 2 is a schematic section of a structural example of a first surface in an inner surface of the disclosed culture bag according to an embodiment.

The fine structure of the first surface may be any fine structure without being particularly limited, and may preferably be a structure having a regular pattern in terms or reliably suppressing the occurrence of foaming and achieving highly efficient culture. Specifically, as illustrated in FIG. 2, the fine structure of the first surface 101 may preferably be a concave-convex structure (first concave-convex structure) having a concave-convex pattern with a height (h1) of 200 nm or more and less than 1 mm, a width (w1) of 200 nm or more and less than 1 mm, and a pitch (p1) of 200 nm or more and less than 1 mm. Further, when the fine structure of the first surface 101 is the aforementioned concave-convex structure, the height (h1) thereof may preferably be 5 μm or more and 50 μm or less, the width (w1) thereof may preferably be 5 μm or more and 40 μm or less, and the pitch (p1) thereof may preferably be 10 μm or more and 80 μm or less, from the same point of view as above.

Further, the fine structure of the first surface may be a structure having the aforementioned concave-convex patterns in an arbitrary one direction (so-called striped concave-convex structure) or may be a structure having the aforementioned concave-convex patterns in arbitrary two directions substantially orthogonal to each other (so-called grid concave-convex structure), with the grid concave-convex structure being preferred. The fine structure of the first surface being a grid concave-convex structure allows for efficiently taking gas present in the culture space into the concave portions during oscillation culture, to thereby efficiently provide desired gas components (for example, oxygen) to the culture targets.

Here, when the fine structure of the first surface employs a grid concave-convex structure, the height, the width, and the pitch of one concave-convex pattern in one direction may all be the same as or may be different from at least one of the height, the width, and the pitch of the other concave-convex pattern in the other direction.

Further, when the fine structure of the first surface is the aforementioned concave-convex pattern, the aspect ratio h1/w1 may preferably be 0.5 or more. The aspect ratio being 0.5 or more allows for efficiently taking gas present in the culture space into the concave portions during oscillation culture, to thereby more efficiently provide desired gas components (for example, oxygen) to the culture targets. From the same point of view, the aspect ratio h1/w1 may preferably be 0.7 or more, and further preferably be 0.9 or more. Further, the aspect ratio h1/w1 may preferably be 10 or less, without being particularly limited.

—Second Surface—

The second surface in the inner surface of the culture bag of this embodiment is formed of a structure different from that of the first surface.

The structure of the second surface is not particularly limited as long as being different from that of the first surface, and may be formed of, for example, an arbitrary structure such as a fine structure or a plane structure (structure of an unfaced sheet material). The "structure different from that of the first surface" herein includes, for example, a structure having a concave-convex pattern similar to that of the first surface but different from that of the first surface at least in any of the height, width, and pitch thereof.

Figure 3:
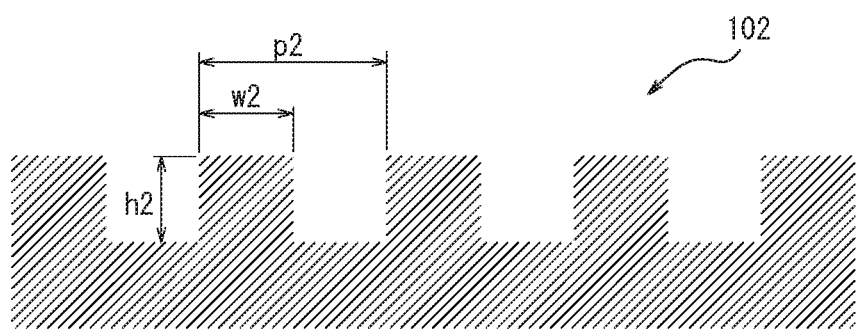
FIG. 3 is a schematic section of a structural example of a second surface in an inner surface of the disclosed culture bag according to an embodiment.

In particular, the structure of the second surface may preferably be a fine structure having a regular pattern in terms of more reliably suppressing the occurrence of foaming and achieving highly efficient culture. Specifically, as illustrated in FIG. 3, the structure of the second surface 102 may preferably be a concave-convex structure (second concave-convex structure) having a concave-convex pattern with a height (h2) of 200 nm or more and less than 1 mm, a width (w2) of 200 nm or more and less than 1 mm, and a pitch (p2) of 200 nm or more and less than 1 mm. Further, when the second surface 102 has a fine structure of the aforementioned concave-convex structure, the height (h2) may further preferably be 5 μm or more and 50 μm or less, the width (w2) may further preferably be 5 μm or more and 40 μm or less, and the pitch (p2) may further preferably be 10 μm or more and 80 μm or less.

Further, when the second surface has a concave-convex structure having the aforementioned concave-convex pattern, the structure may have the aforementioned concave-convex patterns in an arbitrary one direction (so-called striped concave-convex structure) or may have the aforementioned concave-convex patterns in arbitrary two directions substantially orthogonal to each other (so-called grid concave-convex structure), with the grid concave-convex structure being preferred for the structure of the second surface. The structure of the second surface being a grid concave-convex structure allows for efficiently taking gas present in the culture space into the concave portions during oscillation culture, to thereby efficiently provide desired gas components (for example, oxygen) to the culture targets.

Here, when the second surface has a structure of a grid concave-convex structure, the concave-convex pattern in one direction may have the same height, width, and pitch as those of the concave-convex pattern in the other direction, or may be different therefrom at least in any of the height, width, and pitch thereof.

Further, when the structure of the second surface is the aforementioned concave-convex structure, the aspect ratio h2/w2 may preferably be 0.5 or more. The aspect ratio being 0.5 or more allows for efficiently taking gas present in the culture space into the concave portions during oscillation culture, to thereby more efficiently provide desired gas components (for example, oxygen) to the culture targets. From the same point of view, the aspect ratio h2/w2 may preferably be 0.7 or more, and further preferably be 0.9 or more. Further, the aspect ratio h2/w2 may preferably be 10 or less, without being particularly limited.

—Additional Surface—

In the culture bag of this embodiment, the inner surface that comes into contact with a culture fluid may include one or more of additional surfaces different in structure from the aforementioned first surface and second surface.

<Arrangement of First Surface and Second Surface>

The culture bag of this embodiment may preferably include one or more of the first surfaces and the second surfaces alternately adjacent to each other. The first surfaces and the second surfaces may alternately be arranged, so as to make nonuniform the magnitude and the orientation of the flow of the culture fluid, to thereby further improve agitation performance.

Figure 4A:
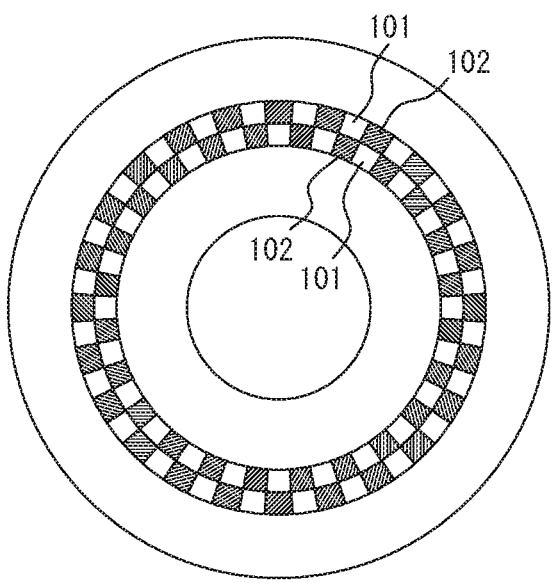
FIGS. 4A to 4D each are a schematic diagram of an exemplary arrangement of the first surfaces and the second surfaces in an inner surface of the disclosed culture bag according to an embodiment.
Figure 4B:
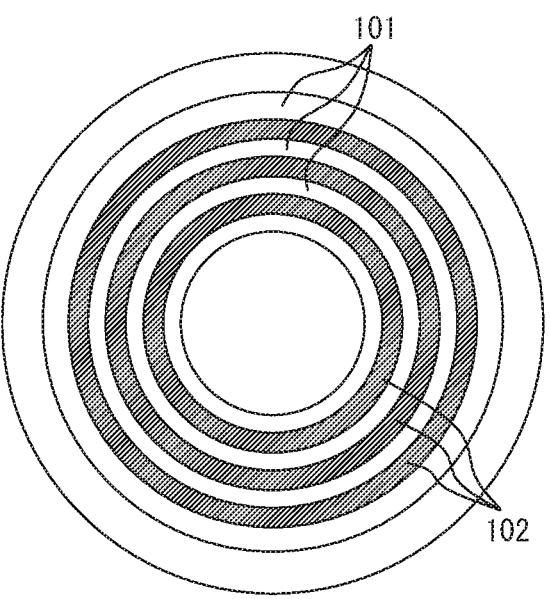
Figure 4C:
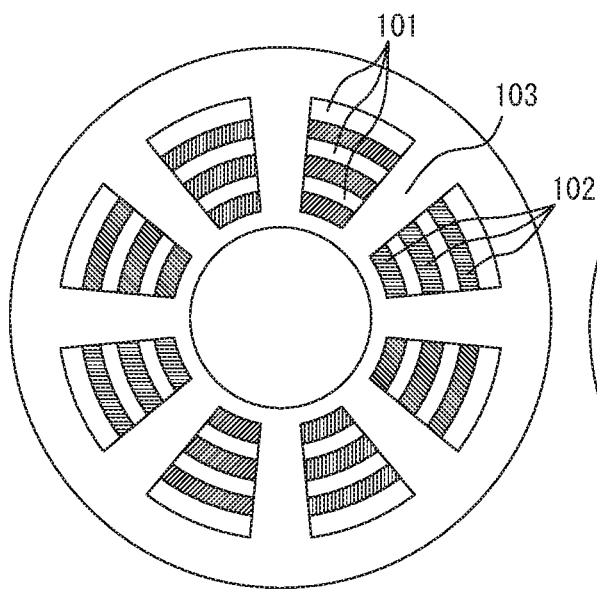
Figure 4D:
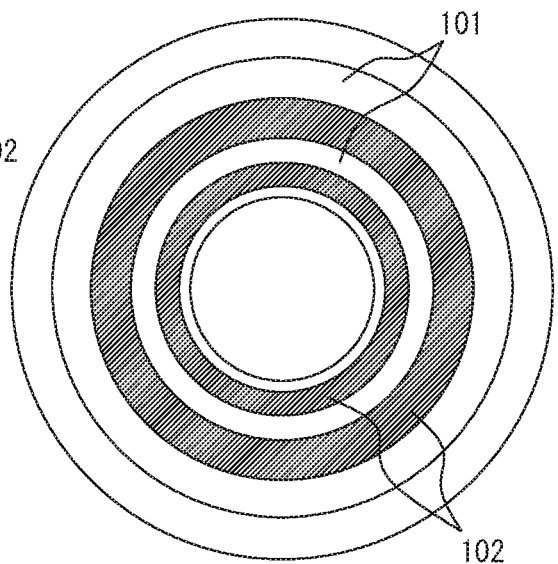

In below, aspects of arrangement of the first surface and the second surface are illustrated by way of example, in a case where the culture bag of this disclosure includes a doughnut-shaped culture space. For example, as illustrated in FIG. 4A, one or more of the first surfaces 101 and one or more of the second surfaces 102 may be arranged as alternately adjacent to each other while forming a plurality of rows (two rows in FIG. 4A) of adjacent concentric circles, to thereby form a checkered pattern. Further, as an application of FIG. 4B, the plurality of concentric circles adjacent to one another may be intermittently continued in the circumferential direction of the doughnut (FIG. 4C); in this case, the portions where the concentric circles are discontinued constitute a third surface 103. Furthermore, as an application of FIG. 4B, the concentric circles may be different from one another in width in the radial direction of the doughnut (FIG. 4D).

<Manufacture of Culture Bag>

The method of manufacturing the culture bag of this embodiment is not particularly limited. The culture bag of this embodiment may be manufactured by: preparing two sheet-like bag base materials; molding each of the bag base materials with a mold so as to eventually obtain a desired three-dimensional culture space; and integrating the two bag materials thus molded facing to each other. The aforementioned exemplary method of manufacturing a culture bag is explained in below.

—Bag Base Material—

Biocompatible materials (materials non-toxic to culture targets such as cells) are preferred as the bag base material, which may include, for example: polyolefin resins such as polypropylene and polyethylene; vinyl resins such as polyvinyl acetate, polyvinyl alcohol, polyvinyl chloride, ethylene vinylalcohol copolymer resin, and ethylene vinylacetate copolymer resin; cycloolefin resins such as cycloolefin polymer (COP) and cycloolefin copolymer (COC); thermoplastic resins such as polystyrene; polyethylene terephthalate; polyurethane; polyamide; polymethyl methacrylate; and polycarbonate; ultra-violet curable resin such as acrylic resin; and an arbitrary electron-beam curable resin.

Further, the sheet-like bag base material may be formed of the aforementioned resin sheet with a nylon sheet laminated thereon. Alternatively, the sheet-like bag base material may be a laminate body having three or more layers with a sheet made of ethylene vinylalcohol copolymer (EVOH) layered in the middle.

—Molding of Bag Base Material—

Exemplary methods of molding the sheet-like bag base material may include, without being particularly limited, injection molding, blow molding, and compression molding, with compression molding being particularly preferred as the bag base material in terms of allowing the bag material to be molded with a uniform force and of eliminating the need for preparing a plurality of molds (a male mold and a female mold).

The mold to be used for the molding may be worked in advance into a structure inverted from a shape capable of eventually obtaining a desired three-dimensional culture space and from a structure to be formed on the inner surface of the culture bag to be eventually obtained. The fine structure may be processed in the mold using, for example, a single crystal diamond bite.

In molding, the bag material and/or mold may be heated in order to increase moldability. The bag material may be heated by, for example, a near infrared or far infrared halogen heater. Meanwhile, the mold may be heated by, for example, a cartridge heater embedded within the mold.

—Integration—

Then, the two molded bag base materials taken off from the mold are integrated as being brought to face each other so as to define a desired three-dimensional culture space therebetween. The molds may each have non-molding parts which serve as contact surfaces, and the surfaces may be thermally fusion-bonded (heat sealed) or bonded with an arbitrary adhesive, for example, to thereby integrate the molds. This way allows the culture bag to be manufactured.

Rather than using two bag base materials to manufacture a culture bag, a single bag base material may be properly molded and folded, for example, so as to be integrally formed.

(Culture Apparatus)

The disclosed culture apparatus according to an embodiment (which may also be referred to as "culture apparatus of this embodiment" in below) is provided with the aforementioned culture bag. The culture apparatus of this embodiment, which includes the aforementioned culture bag, is capable of suppressing the occurrence of foaming while performing a culture with high efficiency. In performing a culture with the culture apparatus of this embodiment, the types of the culture targets (e.g., cells), the configuration and arrangement of the first surface and the second surface provided to the inner surface of the culture bag, and the oscillation conditions may properly be combined.

Further, the culture apparatus of this embodiment may further include, for example, a culture fluid supply mechanism, a culture fluid recovery mechanism, an oscillating mechanism, and a timer mechanism, as long as being the apparatus being provided with the aforementioned culture bag.

EXAMPLES

Next, the present disclosure is more specifically described with reference to Example and Comparative Example. However, the present disclosure is not limited to Examples in below.

The culture bags fabricated in Example and Comparative Example were evaluated for the occurrence of foaming and culture efficiency, according to the following procedure.

(Evaluation of Occurrence of Foaming)

A fabricated culture bag accommodating a 500 mL culture fluid was horizontally installed. The culture fluid accommodated in the culture bag was defined to have: a density of 1007.5 kg/m$^3$; a viscosity of $1.7757e^{-6}$ m$^2$/s; and a surface tension of 0.0602 N/m. Then, the culture bag was horizontally turned (oscillated) with a turning radius of 50 mm and a turning speed (number of rotations) of 20 rpm, so as to visually observe the occurrence of foaming in the culture fluid at that time.

(Evaluation of Culture Efficiency)

The velocity distribution of the culture fluid that flows when the culture bag is oscillated as described above was obtained through simulation. Specifically, a graph of velocity distribution was created in which: the abscissa shows the average velocity of the flowing culture fluid per one cycle for each unit of account; and the ordinate represents a rate (corresponding to the probability of occurrence) of the flowing culture fluid with the entire unit of account being defined as 1. In the aforementioned graph, the broader the peak shape, the more the amount of flow varies, which means that the agitation performance is favorable, leading to high culture efficiency.

Example 1

<Preparation of Mold>

An aluminum alloy sheet (A7075) was prepared as the mold material. This alloy sheet was processed into a shape having a contour of the upper half of a doughnut-like shape, to thereby fabricate a mold A. Separately from the mold A, the aforementioned alloy sheet was processed into a shape having a contour of the upper half of a doughnut-like shape, in which a flat portion with a width of 20 mm in the radial direction was formed by an ultra precision machine and then the portion was processed into two different fine concave-convex structures using a single crystal diamond bite, to thereby fabricate a mold B. Here, the two different fine concave-convex structures mentioned above are configured to have a structure inverted from a structure to be formed in the inner surface of the culture bag to be eventually obtained.

<Fabrication of Culture Bag>

The culture bag was fabricated by compression molding using the aforementioned molds.

Specifically, first, as the material for the bag base material, a 0.3 mm-thick sheet of linear low density polyethylene (LLDPE) (which may also be simply referred to as "resin sheet" in below) was prepared. The aforementioned resin sheet was installed in a chamber so as to partition the chamber into an upper chamber and a lower chamber, with the mold A being installed in the lower chamber. Next, the upper chamber and the lower chamber were each made into a vacuum state, and heated the resin sheet to 150° C. and the mold A to 230° C., respectively. Then, pressure in the upper chamber was returned to the atmospheric pressure, and the resin sheet softened due to the heating was arranged along the mold A. After that, compressed air of 0.31 MPa was supplied from the upper chamber side so as to press the resin sheet to the mold A. Thereafter, with the supply of compressed air being continued, the resin sheet was cooled to 50° to be solidified, and pressures in the upper and lower chambers are each returned to the atmospheric pressure. Then, the sheet was taken off from the mold A to thereby obtain a bag material A. Further, a bag material B was similarly obtained in the same manner as above except using the mold B in place of the mold A.

Then, the bag material A and the bag material B were brought to face each other so as to define a doughnut-like space therebetween, and the contact surfaces were heat sealed to integrate the both, to thereby fabricate a culture bag.

Figure 5:
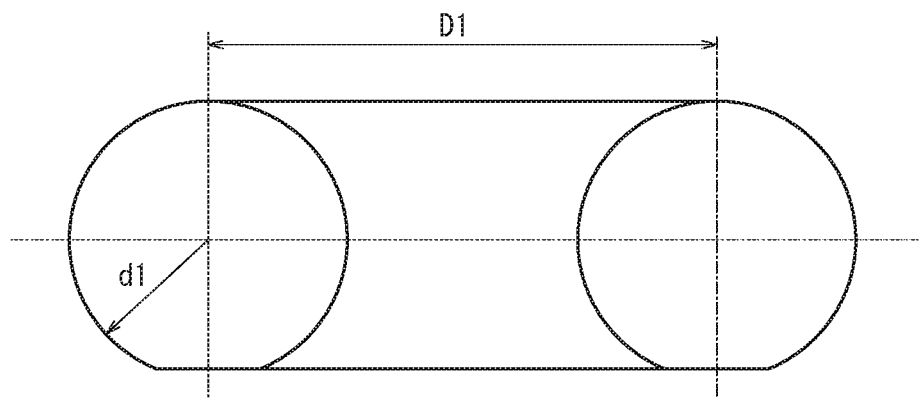
FIG. 5 is a schematic section of the disclosed culture bag according to Example.
Figure 6:
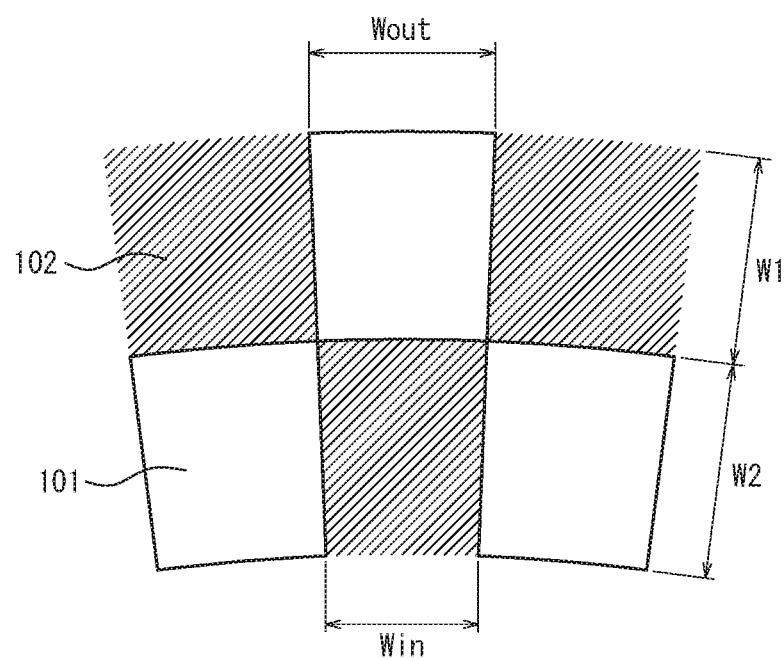
FIG. 6 is a partially enlarged schematic section of the inner surface of the disclosed culture bag according to Example.
Figure 7A:
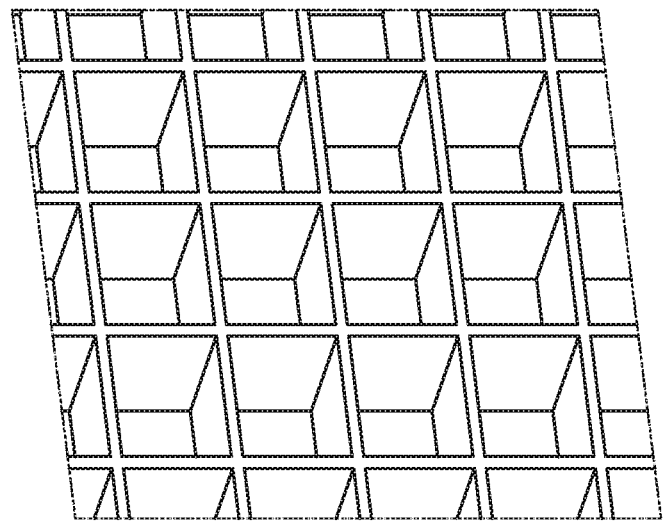
FIGS. 7A and 7B each are a schematic diagram illustrating a grid fine concave-convex structure in an inner surface of the disclosed culture bag according to Example.
Figure 7B:
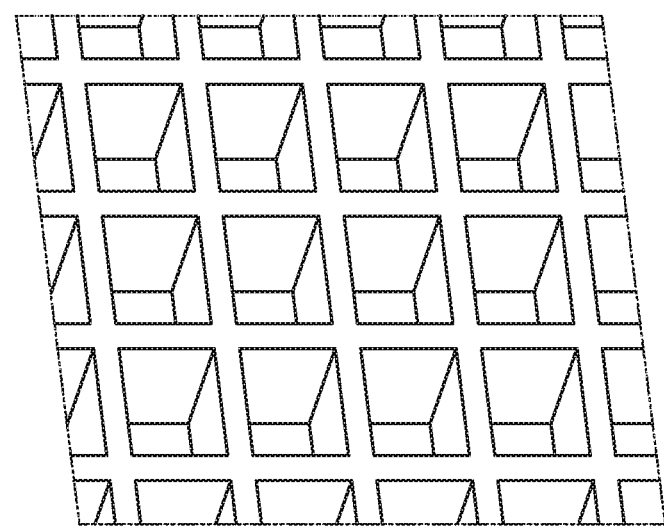

As illustrated in FIG. 5, the culture bag fabricated in Example 1 had a doughnut-like culture space with a center diameter D1 of 180 mm, and the flow path of the culture fluid had a substantially circular cross section with a radius d1 of 30 mm. Further, the bag base material B at the bottom side in use had one or more of the first concave-convex structures and one or more of the second concave-convex structures arranged as alternately adjacent to each other while forming two rows of adjacent concentric circles, to thereby form a checkered pattern as illustrated in FIG. 4A. As to the checkered pattern, each row had a width (W1 or W2) of 10 mm in the radial direction of the doughnut, each concave-convex structure forming the outermost concentric circle had a width ($W_{out}$) of 10 mm in the circumferential direction of the doughnut, and each concave-convex structure forming the innermost concentric circle had a width ($W_{in}$) of 7.85 mm in the circumferential direction of the doughnut (see FIG. 6). Further, in the culture bag fabricated, the first concave-convex structure formed a grid concave-convex structure having concave-convex patterns each with a height (h1) of 20 μm, a width (w1) of 10.7 μm, and a pitch (p1) of 50.7 μm in two directions orthogonal to each other, and the second concave-convex structure formed a grid concave-convex structure having concave-convex patterns each with a height (h2) of 30 μm, a width (w2) of 33.6 μm, and a pitch (p2) of 63.6 μm in two directions orthogonal to each other. For reference, FIG. 7A illustrates a schematic diagram of the first concave-convex structure, and FIG. 7B illustrates a schematic diagram of the second concave-convex structure.

Then, the occurrence of foaming in the culture bag fabricated in Example 1 was visually observed according to the aforementioned procedure. As a result, the occurrence of foaming was hardly observed. Significant reduction of foaming was confirmed in Example 1, as compared with a conventional culture bag provided with baffles.

Figure 8:
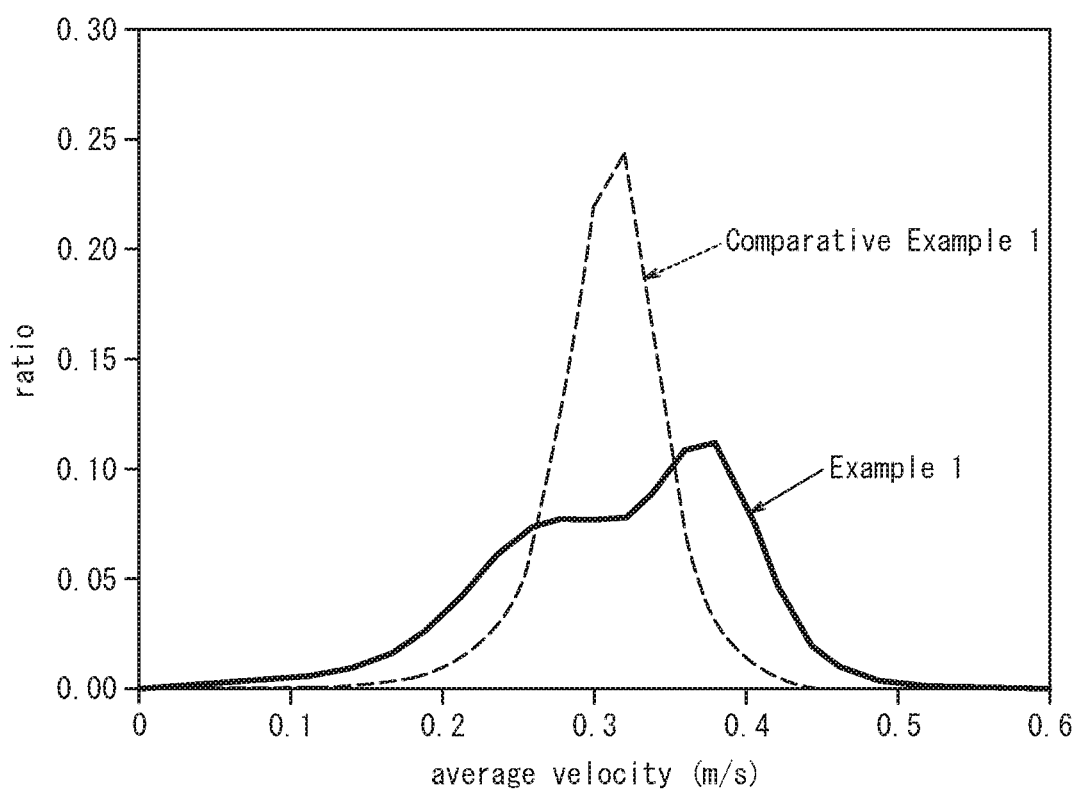
FIG. 8 is a graph illustrating velocity distributions of culture fluids that flow in the culture bags of Example and of Comparative Example when oscillated.

Further, for evaluating the culture efficiency, FIG. 8 illustrates a graph of velocity distribution in Example 1 created according to the aforementioned procedure.

Comparative Example 1

In place of the mold B, the mold C, which was the same as the mold B except in that the mold C had no fine concave-convex structure processed therein with a single crystal diamond bite. Then, similarly to Example 1, the bag base material A was obtained and the bag base material C (corresponding to the bag base material B of Example 1) was obtained to thereby fabricate a culture bag.

Here, the culture bag fabricated in Comparative Example 1 had a doughnut-like culture space with a center radius D1 of 180 mm and the flow path of the culture fluid had a substantially circular cross section with a radius d1 of 30 mm. However, the inner surfaces of the bag base material A and the bag base material C in the culture bag fabricated in Comparative Example 1 all had a uniform structure.

The occurrence of foaming in the culture bag fabricated in Comparative Example 1 was visually observed according to the aforementioned procedure. As a result, the occurrence of foaming was hardly identified.

Further, for evaluating the culture efficiency, FIG. 8 illustrates a graph of velocity distribution in Comparative Example 1 created according to the aforementioned procedure.

As can be understood from FIG. 8, a large fraction of the average velocities of Comparative Example 1 was found in the vicinity of 0.3 m/s with the magnitudes of flow being uniformly distributed as a whole, whereas in Example 1, the average velocities were distributed in a range of 0.1 to 0.5 m/s, with the magnitudes of flow being nonuniform. That is, the culture bag of Example 1, which has different surface structure regions adjacent to each other at least in part of the inner surface, can be found to improve, when accommodating a culture fluid therein and oscillating the same for performing a culture, agitation performance while performing a culture with high efficiency.

INDUSTRIAL APPLICABILITY

The present disclosure can provide a culture bag capable of suppressing the occurrence of foaming when oscillating the culture fluid to perform a culture, and performing a culture with high efficiency, and a culture apparatus including the culture bag.

The invention claimed is:

1. A culture bag comprising a culture space accommodating a culture fluid, wherein:
    the culture bag has an inner surface that comes into contact with the culture fluid to be accommodated therein, the inner surface including, at least in part thereof, a first surface formed of a fine structure and a second surface formed of a structure different from that of the first surface,
    wherein the fine structure of the first surface has a first concave or convex pattern with a height h1 of 5 μm or more and 50 μm or less, a width w1 of 5 μm or more and 40 μm or less, and an aspect ratio h1/w1 of 0.5 or more and 10 or less, and
    wherein the structure of the second surface has a second concave or convex pattern with a height h2 of 5 μm or more and 50 μm or less, a width w2 of 5 μm or more and 40 μm or less, and an aspect ratio h2/w2 of 0.5 or more and 10 or less.

2. The culture bag according to claim 1, wherein the first concave or convex pattern has a pitch p1 of 200 nm or more and less than 1 mm.

3. The culture bag according to claim 1, wherein the second concave or convex pattern has a pitch p2 of 200 nm or more and less than 1 mm.

4. The culture bag according to claim 1, wherein more than one of the first surfaces and more than one of the second surfaces are alternately adjacent to each other.

5. The culture bag according to claim 1, wherein the culture space allows the culture fluid to circulate therein.

6. The culture bag according to claim 1, wherein the culture space has a donut shape.

7. The culture bag according to claim 6, wherein the doughnut shape has an oval shape, or
    a shape defined by one or more arcs and one or more line segments in a cross-sectional area of the culture space, wherein
    the cross-sectional area is taken along a line perpendicular to a circulating direction of the culture fluid.

8. The culture bag according to claim 6, wherein the doughnut shape has an oval shape, or
    a shape defined by one or more arcs and one or more line segments formed by a main circulation path of the culture fluid.

9. The culture bag according to claim 6, further comprising:
    a plurality of first surfaces and a plurality of second surfaces, wherein
    the first surfaces and the second surfaces are arranged alternately adjacent to each other while forming a plurality of rows of adjacent concentric circles, to thereby form a checkered pattern.

10. The culture bag according to claim 6, wherein the first surface forms a plurality of concentric circles, the second surface forms a plurality of concentric circles, and wherein the concentric circles formed by the first surface and the concentric circles formed by the second surface are arranged alternately adjacent to each other.

11. The culture bag according to claim 10, wherein the concentric circles formed by the first surface and the concentric circles formed by the second surface are intermittently continuous in the circumferential direction of the doughnut shape.

12. The culture bag according to claim 10, wherein the concentric circles formed by the first surface are different from one another in width in the radial direction of the doughnut shape, and wherein the concentric circles formed by the second surface are different from one another in width in the radial direction of the doughnut shape.

13. A culture apparatus comprising the culture bag according to claim 1.

14. The culture bag according to claim 1, wherein the culture space has a rectangular shape.

15. The culture bag according to claim 1, wherein the height h1 is different from the height h2, the width w1 is different from the width w2, and the pitch p1 is different from the pitch p2.

16. The culture bag according to claim 1, wherein the aspect ratio h1/w1 is 0.7 or more and 10 or less.

17. The culture bag according to claim 1, wherein the aspect ratio h1/w1 is 0.9 or more and 10 or less.

18. The culture bag according to claim 1, wherein the aspect ratio h2/w2 is 0.7 or more and 10 or less.

19. The culture bag according to claim 1, wherein the aspect ratio h2/w2 is 0.9 or more and 10 or less.

\* \* \* \* \*